United States Patent

Claussner et al.

Patent Number: 5,108,996
Date of Patent: Apr. 28, 1992

[54] 19-NOR-3-KETO STEROIDS

[75] Inventors: Andre Claussner, Villemomble; Jacques Leclaire, Massy; Lucien Nedelec, Le Raincy; Daniel Philibert, La Varenne Saint Hilaire, all of France

[73] Assignee: Roussel Uclaf, Paris, France

[21] Appl. No.: 497,562

[22] Filed: Mar. 21, 1990

[30] Foreign Application Priority Data

Mar. 22, 1989 [FR] France .................. 89 03742

[51] Int. Cl.$^5$ ............... C07J 43/00; A61K 31/565
[52] U.S. Cl. .................. 514/176; 540/101; 540/107; 540/111; 544/294
[58] Field of Search ............ 514/177, 176; 540/107, 540/109, 111, 94, 101; 544/294

[56] References Cited

FOREIGN PATENT DOCUMENTS 263213 4/1988 European Pat. Off. .

OTHER PUBLICATIONS

Jacobsen, J. Med. Chem 1990 33 1145-1151.

Primary Examiner—Mukund J. Shah
Assistant Examiner—E. C. Ward
Attorney, Agent, or Firm—Bierman and Muserlian

[57] ABSTRACT

A compound selected from the group consisting of a compound of the formula

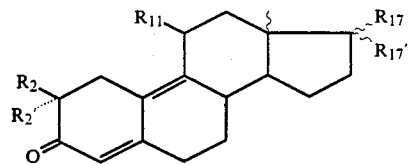

wherein $R_2$ and $R'_2$ are individually hydrogen or methyl, $R_{11}$ is an organo of 1 to 18 carbon atoms optionally containing at least one heteroatom with the atom adjacent to the 11-carbon atom being a carbon, the wavy lines at the 13 and 17-positions indicate that when the 13-methyl is $\alpha$, $R'_{17}$ group is $\beta$ and $R_{17}$ is $\alpha$ and when the 13-methyl is $\beta$, $R_{17}$ is $\beta$ and $R'_{17}$ is $\alpha$, $R_{17}$ is —OH or acyloxy of 1 to 18 carbon atoms and $R'_{17}$ is

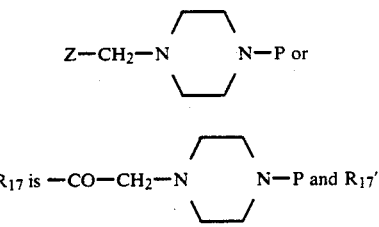

is hydrogen or —OH or acyloxy of 1 to 18 carbon atoms, Z is selected from the group consisting of a single bond, alkylene of 1 to 5 carbon atoms and alkenylene and alkynylene of 2 to 5 carbon atoms and P is selected from the group consisting of pyrimidinyl and pyridyl optionally substituted with 1 or 2 individual members of the group consisting of amino, alkylamino and dialkylamino of 1 to 4 alkyl carbon atoms and (B aminated 5- or 6-membered heterocycle optionally substituted with alkyl of 1 to 3 carbon atoms) and its non-toxic, pharmaceutically acceptable acid addition salts having anti-inflammatory and anti-oxidant activity.

18 Claims, No Drawings

19-NOR-3-KETO STEROIDS

STATE OF THE ART

Related prior art includes PCT patent applications No. WO.A. 8,701,706 and WO.A. 8,707,895 and U.S. Pat. No. 3,483,233.

OBJECTS OF THE INVENTION

It is an object of the invention to provide the novel compounds of formula I and their non-toxic, pharmaceutically acceptable acid addition salts and a novel process and intermediates for their preparation.

It is another object of the invention to provide novel anti-inflammatory compositions and a method of treating inflammation in warm-blooded animals.

These and other objects and advantages of the invention will become obvious from the following detailed description.

THE INVENTION

The novel compounds of the invention are selected from the group consisting of a compound of the formula

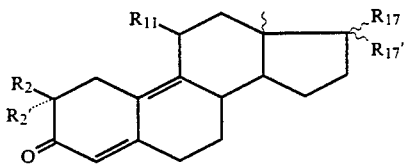

wherein $R_2$ and $R_2'$ are individually hydrogen or methyl, $R_{11}$ is an organo of 1 to 18 carbon atoms optionally containing at least one heteroatom with the atom adjacent to the 11-carbon atom being a carbon, the wavy lines at the 13 and 17-positions indicate that when the 13-methyl is $\alpha$, $R_{17}'$ group is $\beta$ and $R_{17}$ is $\alpha$ and when the 13-methyl is $\beta$, $R_{17}$ is $\beta$ and $R_{17}'$ is $\alpha$, $R_{17}$ is —OH or acyloxy of 1 to 18 carbon atoms and $R_{17}'$ is

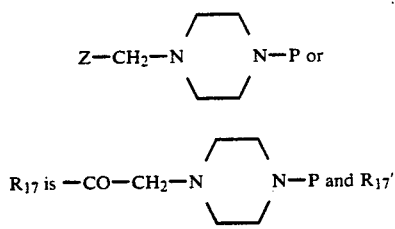

is hydrogen or —OH or acyloxy of 1 to 18 carbon atoms, Z is selected from the group consisting of a single bond, alkylene of 1 to 5 carbon atoms and alkenylene and alkynylene of 2 to 5 carbon atoms and P is selected from the group consisting of pyrimidinyl and pyridyl optionally substituted with 1 or 2 individual members of the group consisting of amino, alkylamino and dialkylamino of 1 to 4 alkyl carbon atoms and (B aminated 5-or 6-membered heterocycle optionally substituted with alkyl of 1 to 3 carbon atoms) and its non-toxic, pharmaceutically acceptable acid addition salts.

$R_{11}$ may be a saturated or unsaturated aliphatic of 1 to 18 carbon atoms and examples are methyl, ethyl, propyl, iso-propyl, butyl, iso-butyl, tert-butyl, n-pentyl, n-hexyl, 2-methylpentyl, 2,3-dimethylbutyl, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl, nonyl, 2,4-dimethylheptyl and n-decyl; vinyl, isopropenyl, allyl, 2-methylallyl and isobutenyl. The said aliphatics may be substituted such as thioalkyl such as thiomethyl or thioethyl and substituted with one or more halogens such as fluorine, chlorine, bromine, iodine or with substituted amino radicals such as dimethylamino.

$R_{11}$ can also be aryl such as phenyl or aralkyl such as benzyl which aromatics can be ortho-, meta- or para-substituted with one or more alkyls, preferably of 1 to 4 carbon atoms; one or more alkoxys, preferably of 1 to 4 carbon atoms such as methoxy, ethoxy, propoxy, isopropoxy, butoxy, isobutoxy, tert-butoxy; alkenyloxy such as vinyloxy or allyloxy; one or more halogens, preferably chlorine or fluorine; one or more groups selected from the hydroxyl and trifluoromethyl and alkylthio of 1 to 4 carbon atoms optionally oxidized in the form of a sulfoxide or sulfone such as methylthio, ethylthio; an acyl such as formyl, acetyl, propionyl, butyryl, or benzoyl, preferably acetyl. The aryl or aralkyl may be substituted with a combination of these different radicals such as, for example, 3-fluoro-4-dimethylaminophenyl.

$R_{11}$ can also be a heterocyclic aryl optionally substituted with the different radicals envisaged above, examples of which are thienyl, furyl, isothienyl, isofuryl, thiazolyl, isothiazolyl, oxazolyl, isoxazolyl, thiadiazolyl, pyridyl or piperidyl and heterocycles known to those skilled in the art.

$R_{11}$ can also be cycloalkyl such as cyclopropyl, cyclobutyl, cyclopentyl or cyclohexyl, or cycloalkenyl such as cycobutenyl or cyclopropenyl.

$R_{11}$ can also represent a group containing an aryl ring substituted either with an amine function optionally substituted with one or two alkyls of 1 to 8 carbon atoms, or with an amino incorporated in a heterocycle optionally containing another hetero atom selected from the group composed of oxygen, nitrogen and sulfur such as morpholino or piperidyl.

The aryl ring is preferably phenyl and a substituent on the aryl ring is also possibly a [(substituted) amino]-alkyl such as dimethylaminomethyl or dimethylaminoethyl; or a [(substituted) amino]-alkoxy such as dimethylaminoethoxy Groups containing a silicon atom such as a (trimethylsilyl)-phenyl may also be mentioned. The groups mentioned above containing a nitrogen atom can be oxidized.

Generally speaking, products in which $R_{11}$ contains a hetero atom, preferably nitrogen or sulfur, are preferred.

When $R_{17}$ is acyloxy, the latter can be a derivative of a saturated or unsaturated aliphatic or cycloaliphatic carboxylic acid, and particularly an alkanoic acid such as acetic acid, propionic acid, butyric acid or isobutyric acid, valeric acid or undecylic acid; a hydroxyalkanoic acid such as hydroxyacetic acid; a cycloalkanecarboxylic acid or (cycloalkyl)alkanoic acid such as cyclopropane-carboxylic acid, cyclopentanecarboxylic acid or cyclohexanecarboxylic acid, cyclopentylcarboxylic acid or cyclohexyl acetic or -propionic acid; benzoic acid or phenylalkanoic acid such as phenylacetic acid or phenylpropionic acid; an amino acid such as diethylaminoacetic acid or aspartic acid or formic acid; it is preferably the acyl of acetic acid, propionic acid or buytric acid.

In $R_{17}'$, when Z is an alkylene, it is preferably methylene, ethylene or trimethylene. When Z is an alkenylene, it is preferably vinylene and when Z is an alkynylene, it is preferably ethynylene. When P is substituted with an alkylamino, the alkyl preferably contains from 1 to 4 carbon atoms and examples thereof are methyl, ethyl, n-propyl, isopropyl, n-butyl, isobutyl and tert-butyl amino, with methyl or ethylamino being preferred. When P is substituted with a dialkylamino, the alkyls preferably contain from 1 to 4 carbon atoms and examples are dimethyl, diethyl, or methylethylamino, and when P is substituted with one or two aminated heterocycles, the latter can be a saturated heterocycle, preferably pyrrolidine or piperidine optionally substituted with an alkyl such as methyl, ethyl, propyl or isopropyl, preferably methyl or ethyl, or an unsaturated heterocycle, preferably pyrrole optionally substituted with an alkyl such as methyl. The aminated heterocycle or heterocycles is/are generally linked to P via the nitrogen atom.

In $R_{17}$, when P is substituted with an alkylamino or dialkylamino or with aminated heterocycles, these denote one of the radicals or one of the heterocycles mentioned above; and when $R_{17}'$ is an acyloxy, the latter is preferably a derivative selected from those mentioned above, especially an acyl of acetic acid, propionic acid, butyric acid or benzoic acid.

Examples of suitable acids for the formation of the non-toxic, pharmaceutically acceptable acid addition salts of the compounds of formula I are hydrochloric acid, hydrobromic acid, nitric acid, sulfuric acid, phosphoric acid, acetic acid, formic acid, propionic acid, maleic acid, fumaric acid, succinic acid, tartaric acid, citric acid, oxalic acid, glyoxylic acid and aspartic acid, alkanesulfonic acids such as methane- or ethanesulfonic acid, arylsulfonic acids such as benzene- or p-toluenesulfonic acid and arylcarboxylic acids such as benzoic acid.

Among the preferred compounds of the invention of formula I are those wherein P is pyrimidinyl or pyridyl substituted with two identical or different members selected from dialkylamino or aminated 5- or 6-membered heterocycles, those wherein P is 2,6-bis(1-pyrrolidinyl)-4-pyrimidinyl, 5,6-bis(diethylamino)-2-pyridyl, or 3,6-bis(diethylamino)-2-pyridyl and those wherein the 13-methyl is in the β configuration, those wherein $R_{11}$ is an aryl or aralkyl bearing an amino function:

in which R' and R" are alkyl of 1 to 8 carbon atoms or a primary, secondary or tertiary alkyl of 1 to 8 carbon atoms and containing one or more hetero atoms selected from the group consisting of oxygen, nitrogen and sulfur, including at least one nitrogen atom, or substituted with a heterocycle containing at least one nitrogen atom, those wherein $R_{11}$ is 2-, 3- or 4-pyridyl,

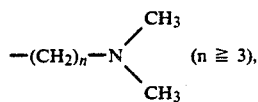

-continued

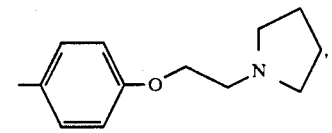

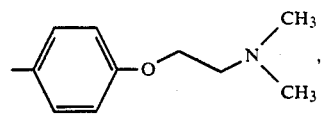

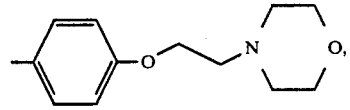

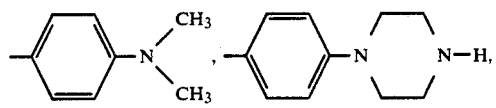

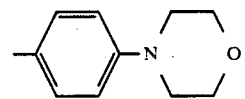

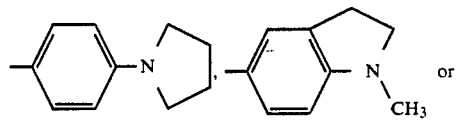

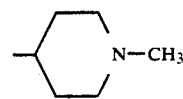

those wherein $R_{11}$ is thienyl or furyl or cycloalkyl of 3 to 6 carbon atoms or phenyl optionally substituted with one or more members selected from hydroxy, halogen, trifluoromethyl, alkyl and alkoxy and alkylthio optionally oxidized in the form of a sulfoxide or sulfone, and those wherein $R_{11}$ is phenyl substituted with a member selected from the group composed of chloro, fluoro, methylthio, methylsulfonyl, methoxy, hydroxy, and allyloxy and acyl such as acetyl. Among the latter,

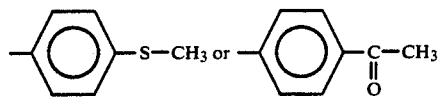

are preferred.

Among other preferred compounds of the invention are those wherein $R_2$ and $R_2'$ each represent hydrogen, those wherein $R_{17}$ is hydroxyl when $R_{17}'$ is

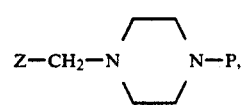

and more especially those for which Z is —C≡C or —CH=CH or —CH$_2$—CH$_2$— when $R_{17}'$ is

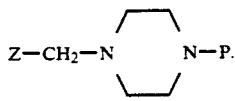

Among specific preferred compounds of the invention are 11β-[4-(dimethylamino)-phenyl]-17α-[3-{4-[2,6-bis(1-pyrrolidinyl)-4-pyrimidinyl]-1-piperazinyl}-1-propynyl]-Δ$^{4,9}$-estradiene-17β-ol-3-one; 11β-[4-(dimethylamino-phenyl]-17α-[3-{4-[5,6-bis(diethylamino)-2-pyridyl]-1-piperazinyl}-1-propynyl]-Δ4,9-estradiene-17β-ol-3-one; 11β-[4-(dimethylamino)-phenyl]-17-α[3-{4-[3,6-bis(diethylamino)-2-pyridyl]-1-piperazinyl}-1-propynyl]-Δ$^{4,9}$-estradien-17β-ol-3-one, 11β-[4-(dimethylamino)-phenyl]-17α-[3-{4-[2,6-bis(1-pyrrolidinyl)-4-pyrimidinyl]-1-piperazinyl}-1-propenyl]-Δ$^{4,9}$-estradien-17β-ol-3-one, 11β-[4-(dimethylamino)-phenyl]-17α-[3-{4-[2,6-bis(1-pyrrolidinyl)-4-pyrimidinyl]-1-piperazinyl}-1-propyl]-Δ$^{4,9}$-estradien-17β-ol-3-one and their salts.

The novel process of the invention for the preparation of a compound of formula I comprises reacting a compound of formula II which is either a compound of the formula

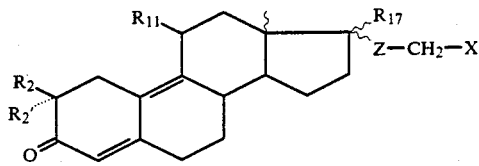

or a compound of the formula

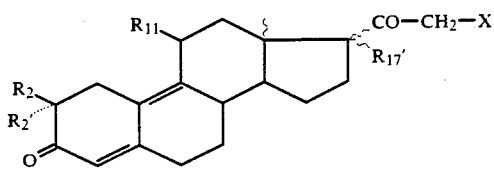

wherein X is halogen and $R_2$, $R_2'$, $R_{11}$, the wavy lines, $R_{17}$, $R_{17}'$ and Z have the above meanings with a compound of the formula

wherein P has the above meaning in a neutral solvent and in the presence of a base, and where appropriate when Z is an alkynylene or alkenylene, the products obtained are subjected to a partial or total hydrogenation reaction and, optionally the products obtained are subjected to the action of an acid to obtain the corresponding salt.

The compounds of formula I are obtained using a compound of formula II selected from either a compound of formula IIa or a compound of formula IIb wherein X is chlorine, bromine or iodine working in a neutral solvent such as dimethylformamide, tetrahydrofuran, methylene chloride, acetonitrile, ethyl ether or acetone in the presence of a base such as an alkali metal carbonate or bicarbonate, preferably sodium or potassium carbonate or bicarbonate, triethylamine or diisopropylethylamine.

Where appropriate, the compounds of formula I containing an alkynylene or alkenylene Z are subjected to a partial or total hydrogenation reaction, for example using hydrogen in the presence of palladium on active charcoal or barium sulfate, in the presence or absence of triethylamine to obtain compounds of formula I having an alkenylene or alkylene as Z.

In a variation of the process of the invention to prepare the compounds of formula I in which $R_2$ and $R_2'$ are hydrogen, $R_{17}$ is hydroxyl and $R_{17'}$ is

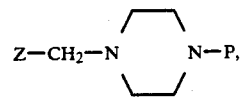

a compound of the formula

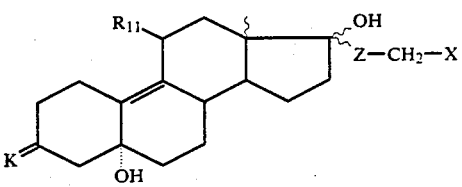

wherein X is halogen and $R_{11}$, the wavy lines and Z have the above meaning and K is a group protecting the ketone is reacted with a compound of the formula

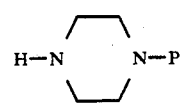

wherein P has the above meaning to obtain a compound of the formula

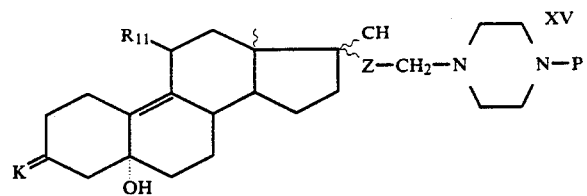

and the latter is then subjected to a dehydration and hydrolysis reaction capable of liberating the 3-keto-Δ$^4$ function, this reaction being preceded or followed by an optionally partial or total hydrogenation when Z is an alkynylene or alkenylene, and optionally the products of formula I are subjected to the action of an acid to obtain the corresponding salt.

According to the variant, the compounds of formula I are obtained by reacting a compound of formula II' with a compound of formula III under the same working conditions as above, and then liberating the 3-keto-Δ$^4$ function, for example by the action of hydrochloric acid. Where appropriate, the product of formula I or the product of formula XV before unblocking of the group K, is subjected to a partial or total hydrogenation reaction performed under the same conditions as above to obtain compounds of formula I having an alkenylene or alkylene as Z.

In a preferred embodiment of the process of the invention and of the variant of the process, the compound of formula II is the compound of formula IIa, namely 17α-(3-bromo-1-propynyl)-11β-[4-(dimethylamino)-phenyl]-Δ$^{4,9}$-estradiene-17β-ol-3-one and the compound of formula II' is 3,3-(ethanediylbisoxy)-17α-(3-bromo-1-propynyl)-11β-[4-(dimethylamino)-phenyl]-Δ$^9$-estrene-5α17β-diol, which are described below and the neutral solvent is acetone, the base is potassium carbonate and the compound of formula III is either 2,4-bis(1-pyrrolidinyl)-6-(1-piperazinyl) pyrimidine:

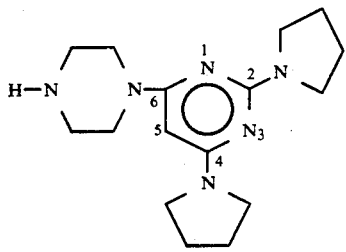

which may be obtained according to the preparation described in Patent Application No. WO 8,701,706 or N,N,N',N'-tetraethyl-6-(1-piperazinyl)-2,3-pyridinediamine

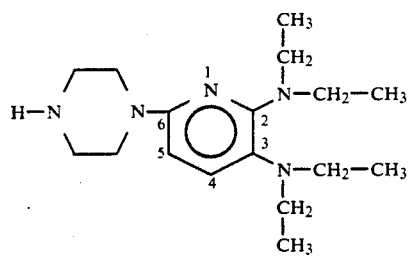

which, although named erroneously, may be obtained according to the preparation described in Patent Application No. WO 8,701,706 or N,N,N',N'-tetraethyl-6-(1-piperazinyl)-2,5-pyridinediamine

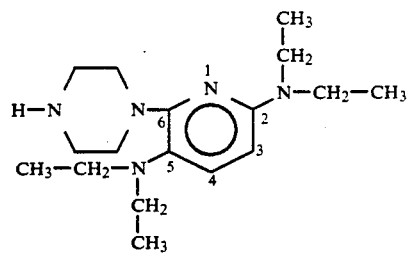

described in French patent application Ser. No. 89-03740, the preparation of which is given later in the experimental part and which, contrary to what is stated, cannot be obtained according to the preparation described in Patent application WO 8,701,706.

The compounds of formula I according to the invention may be obtained in the state of salts by known methods which consist in reacting the compound of formula I with an inorganic or organic acid selected from the group of acids mentioned above.

The novel anti-inflammatory compositions of the invention are comprised of an anti-inflammatorily effective amount of at least one compound of formula I and its non-toxic, pharmaceutically acceptable acid addition salts and an inert pharmaceutical carrier. The composition may be in the form of tablets, dragees, capsules, creams, pomades, suppositories and injectable solutions or suspensions.

Examples of suitable excipients are talc, starch, aqueous or non-aqueous vehicles, fats of animal or vegetable origin, paraffin derivatives, glycols, the various wetting, dispersant or emulsifying agents and preservatives.

The compositions are useful in the treatment of acute inflammation mediated by arachidonic acid derivatives and are advantageous for the treatment of local inflammatory reactions such as oedema, dermatoses, pruritus, the various forms of eczema and solar erythema, or for the treatment of acute inflammatory diseases or chronic inflammatory diseases such as rheumatoid arthritis, psoriasis or multiple sclerosis.

The compositions of the invention also have particularly an antioxidant activity by inhibition of tissue lipid peroxidation, for example in the kidney and heart and especially in the brain and spinal cord and also display a detoxifying activity in acute intoxications associated with the peroxidation of lipids of brain tissues such as the brain or spinal cord. The compositions may be used in the treatment of biological disorders following trauma. Trauma is understood to mean tissue damage in which the generation of lipid peroxides is involved, and which may be produced by a variety of agents, for example physical agents such as contusions, especially cerebal contusions associated or otherwise with local haemorrhage, or chemical agents such as those used in antitumor chemotherapy, for example adriamycin, or such as those used in cancer immunotherapy, for example IL-2 or TNF. They are most especially advantageous in the treatment of cerebral ischaemia, especially in the treatment of cerebral infarction and in the prevention of its recurrence, or in the treatment of drug intoxication produced by chemotherapy or immunotherapy or a combination of the two.

The novel method of the invention for treatment of inflammation in warm-blooded animals, including humans, comprises administering to warm-blooded animals an anti-inflammatorily effective amount of at least one compound of formula I and its non-toxic, pharmaceutically acceptable acid addition salts. The compositions may be administered orally or parenterally such as by intra-muscular, intra-articular or intrathecal injection, and preferably by intravenous injection in a bolus or in continuous perfusion, or locally by topical application to the skin or the mucosae. The usual daily dose is 0.01 to 1 mg/kg depending on the condition being treated, the specific compound used and the method of administration.

The starting compounds of formula II are halogenated derivatives of 19-nor-3-keto steroids which are new products and an object of the invention. The starting compounds of formula IIa are prepared by a procedure of which an example is given later in the Examples. Generally, the compounds of formula IIa may be prepared by the following scheme:

According to the process described in French Patent Application No. 2,433,536, the lithium derivative of the product of the formula.

$$H-Z-CH_2-OR \qquad\qquad IV$$

in which Z has the above meaning and R is either hydrogen or a group protecting the alcohol function is reacted with a steroid of the formula

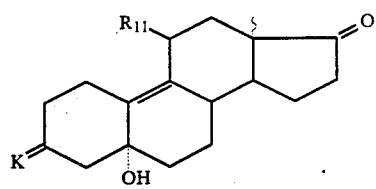

in which $R_{11}$ and the wavy line have the above meaning and K is a group protecting the 3-ketone such as a cyclic acetal to obtain a product of the formula

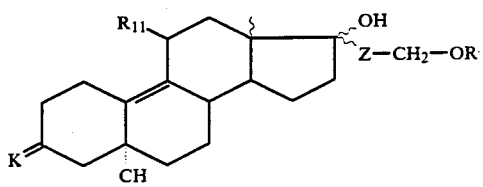

which is subjected to a dehydrating and hydrolytic agent capable of liberating the 3-keto-$^4$ function and, where appropriate, the alcohol function to obtain the product of the formula

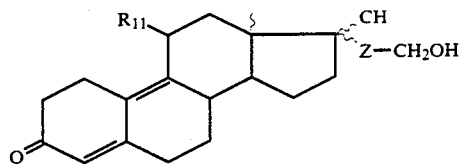

which is subjected, if desired, to a methylating agent after the alcohol functions have been temporarily protected to obtain a product of the formula

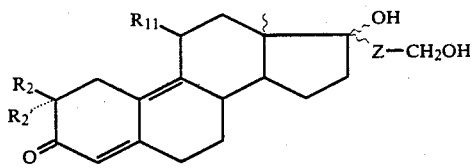

in which at least one of $R_2$ and $R_{2'}$ is methyl, which products of formula VII or VIII are subjected to a halogenating agent to obtain the product corresponding to a product of formula IIa in which $R_{17}$ is hydroxyl.

The products obtained may then be subjected, if desired, to an esterifying agent, for example according to the process described in French Patent Application No. 2,433,536 which introduces an acyl at position 17 only.

The products of formula V as defined above necessary for carrying out the process, are 17-keto steroids obtained from the corresponding $\Delta^{9,11}$-5,10-epoxy steroids which are known products described in Patent No. EP0,057,115. Steroids of formula V having a 13α-methyl are prepared from the 17-keto steroids with a 13β-configuration by the process described in Patent EP 129,499.

Steroids of formula VIII in which $R_2$ and $R_{2'}$ are methyl are prepared from the corresponding steroids of formula VII by the process described in French Patent No. 2,528,434.

The compounds of formula IIb used as starting materials for the process of the invention are 19-nor-3-keto-21-halo steroids which may be prepared from the corresponding 21-hydroxylated steroids by methods known to those skilled in the art or, for example, according to the process described in Patent Application WO 8,701,706. 19-Nor-3-keto-21-hydroxylated steroids having hydrogen or hydroxyl at the 17α-position are known steroids or steroids whose preparation is known to those skilled in the art as described in French Patent No. 2,528,434 and EP Patent No. 129,499. They can also be prepared from the corresponding 17-keto steroids using the processes described in French Patent Applications No. 2,462,445 or No. 2,498,607 and the 17-keto steroids are themselves known products described in French Patent No. 2,522,328 and Patent No. EP 104,387.

The compounds of formula II' used as starting materials are halogenated derivatives of blocked 19-nor-3-keto steroids which are new products and a subject of the invention. The compounds of formula II' are prepared by a procedure of which an example is given later in the Examples. Generally speaking, they are obtained from the products of formula VI in which R is hydrogen which are reacted with a halogenating agent.

Among the preferred new industrial products of formulae II and II' are 17α-(3-bromo-1-propynyl)-11β-[4-(dimethylamino)-phenyl]-$\Delta^{4,9}$-estradien-17β-ol-3-one and 3,3-(ethanediylbisoxy)-17α-(3-bromo-1-propynyl)-11β-[4-(dimethylamino)-phenyl]-$\Delta^9$-estrene-5α,17β-diol.

The compounds of formula XV are new intermediate products, and an object of the invention.

The compounds of formula III used as starting materials for the process of the invention in which P is an unsubstituted or monosubstituted group are prepared by Patent Application No. WO 8,701,706 as well as the compounds of formula III in which P is a disubstituted group such as 2,6-(disubstituted)-4-pyrimidinyl, for example:

2,6-bis(1-pyrrolidinyl)-4-pyrimidinyl

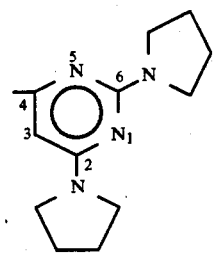

or: 5,6-(disubstituted)-2-pyridyl, for example 5,6-bis(diethylamino)-2-pyridyl

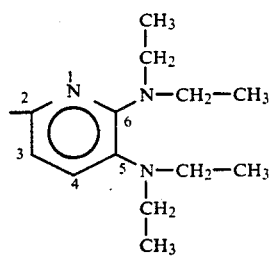

In contrast, the compounds of formula III in which P is a 3,6-(disubstituted)-2-pyridyl, for example 3,6-bis(-diethylamino)-2-pyridyl

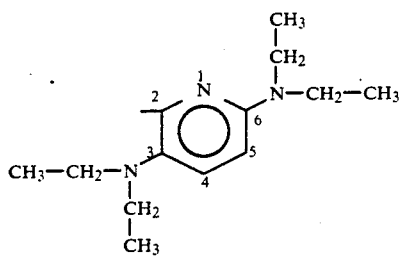

are new products which are prepared as described in French Patent Application No. 8,903,740 by a procedure of which an example of preparation is given later.

These compounds of formula III may be prepared by the following scheme: A product of the formula

IX in which R' is a group protecting the amino function such as acetyl is reacted with a product of the formula

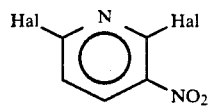

X in which Hal is halogen, preferably chlorine, to obtain a product of the formula

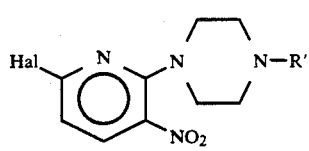

XI which is reacted with a product of the formula

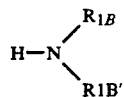

XII in which $R_{1B}$ and $R_{1B'}$ *either have the above meaning for RB and $R_{B'}$*, or are such that either one is a monovalent group protecting the amino function, for example benzyl or trityl, and the other is hydrogen or $R_{1B}$ and $R_{1B'}$ together form a divalent protective group, for example $R_{1B}$ and $R_{1B'}$ together with the nitrogen to which they are attached, form 2,5-dimethylpyrrole to obtain a product of the formula

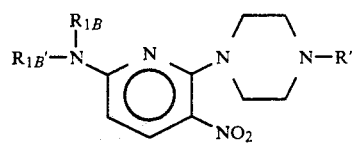

XIII which is subjected to a hydrogenation reaction to obtain a product of the formula

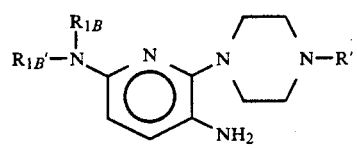

XIV which product, if desired, is either a) subjected to the action of one or two equivalents of a monohalogenated derivative of $R_A$ or of $R_A'$ to obtain a product of the formula

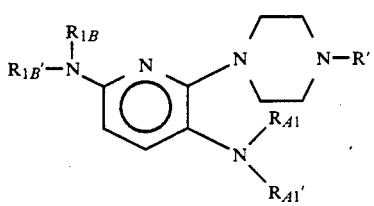

XIV' in which either one of $R_{A1}$ and $R_{A1}'$ is hydrogen and the other is an alkyl or both are the same alkyl or b) subjected to the action of a monohalogenated derivative of $R_A$ or $R_A'$ and then to the action of a monohalogenated derivative of $R_A'$ or of $R_A$ to obtain a product of the formula

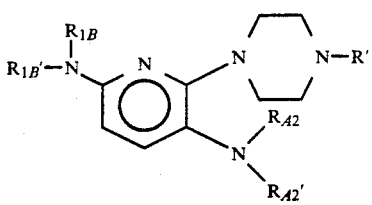

XIV"

in which $R_{A2}$ and $R_{A2}'$ are different alkyls or c) subjected to the action of a dihalogenated derivative of butane or of pentane optionally substituted with an alkyl of 1 to 3 carbon atoms to obtain a product of the formula

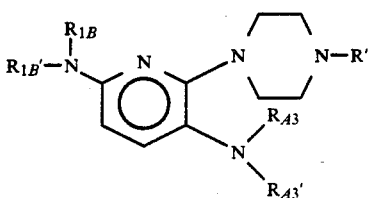

XIV''' in which $R_{A3}$ and $R_{A3}'$, with the atom to which they are attached, form a 5- or 6-membered heterocycle, which products of formulae XIV, XIV', XIV'' or XIV''' are subjected to a reaction of unblocking of the group R' and, where appropriate, of the groups $R_{1B}$ and/or $R_{1B}'$, to obtain the corresponding compounds of formula III.

Among the preferred new products of formula III of the invention are N,N,N'N'-tetraethyl-6-(1-piperazinyl)-2,5-pyridinediamine which, as stated above, cannot be obtained by the preparation described in Patent Application No. WO 8,701,706 and N,N'-dipyrrolidyl-6-(1-piperazinyl)-2,5-pyridinediamine.

In the following examples, there are described several preferred embodiments to illustrate the invention. However, it is to be understood that the invention is not intended to be limited to the specific embodiments.

PREPARATION 1

17α-(3-bromo-1-propynyl)-11β-[4-(dimethylamino)-phenyl]-$\Delta^{4,9}$-estradiene-17β-ol-3-one.

600 mg of 11β-[4-(dimethylamino)-phenyl]-17α-(3-hydroxy-1-propynyl)-$\Delta^{4,9}$-estradien-17β-ol-3-one, described in French Patent Application No. 2,566,779, were dissolved in 6 ml of methylene chloride and 491 mg of carbon tetrabromide and the solution was cooled to −10° C. A solution of 531 mg of triphenylphosphine in 3 ml of methylene chloride was then added dropwise and the mixture was stirred for 20 minutes at −10° C. then placed without further treatment on a column of 15 g of silica. The column was eluted with a 50:50 petroleum ether (b.p. 40°–70° C.)-ethyl acetate mixture to obtain 384 mg of the pure brominated product in the form of a crystallized solid.

PREPARATION 2

3,3-(ethanediylbisoxy)-11β-(4-dimethylaminophenyl)-17α-(3-bromo-1-propynyl)-$\Delta^9$-estrene-5α,17β-diol

STEP A:

3,3-ethanediylbisoxy)-11β-(4-dimethylaminophenyl)-17α-(3-hydroxy-1-propynyl)-$\Delta^9$estrene The procedure was as in the first part of Example 1 of French Patent No. 2,566,779 starting with propargyl alcohol and 3,3-(1,2-ethanediylbisoxy)-11β-(4-dimethylaminophenyl)-$\Delta^9$-estren-5α-ol-17-one.

STEP B:

3,3-(ethanediylbisoxy)-11β-(4-dimethylaminophenyl)-17α-(3-bromo-1-propynyl)-$\Delta^9$-estrene-5α,17β-diol The procedure was as in Preparation 1 starting with 4 g of the product of Step A to obtain an oil which was used without further treatment in Example 6.

PREPARATION 3

N,N,N',N'-tetraethyl-6-(1-piperazinyl)-2,5-pyridinediamine

STEP A:

1-acetyl-4-[6-diethylamino)-3-nitro-2-pyridyl]-piperazine

A solution of 51.22 g of N-acetyl-piperazine in 200 ml of acetonitrile was added over 50 minutes at 0° C. to a mixture of 78 g of 2,6-dichloro-3-nitropyridine, 600 ml of acetonitrile and 66.3 g of potassium carbonate. The mixture was allowed to return to room temperature and was stirred for 75 minutes. The inorganic salts were filtered off and 180 ml of N,N-diethylamine and 76 g of potassium carbonate were added to the filtrate and the mixture was refluxed for 75 minutes. The inorganic salts were filtered off after cooling and the filtrate was evaporated to dryness under reduced pressure. The 166.9 g of residue were crystallized from 200 ml of ethyl acetate to obtain 87.4 g of the expected product melting at 120° C.

STEP B:

N,N,N',N'-tetraethyl-6-(1-piperazinyl)-2,5-pyridinediamine

A mixture of 70 g of the product of Step A, 1500 ml of methanol, 61.5 ml of acetaldehyde and 10 g of activated charcoal containing 10% of palladium was hydrogenated at a maximum pressure of 1250 mbar at 25° C. Approximately 20 liters of hydrogen were absorbed after which the catalyst was filtered off and the filtrate was evaporated to dryness under reduced pressure. The 89.8 g of residue were taken up with 500 ml of n-propanol and 91.3 g of potassium hydroxide pellets and the mixture was refluxed for 3 hours. The cooled solution was poured into 1 liter of ice-cold water and the product was extracted with methylene chloride. The organic solution was washed with saturated sodium chloride solution, dried, filtered and concentrated to dryness under reduced pressure. The 58.9 g of residue were chromatgraphed on silica (eluent: methylene chloride-methanol-ammonia solution (95:5:0.5)) to obtain 48.35 g of the expected product which was used without further treatment.

Analysis: $C_{17}H_{31}N_5$
Calculated: % C 66.84, % H 10.23, % N 22.93.
Found: 66.9, 10.5, 22.6.

EXAMPLE 1

11β-[4-(dimethylamino)-phenyl]-17α-[3-{4-[2,6-bis(1-pyrrolidinyl)-4-pyrimidinyl]-1-piperazinyl}-1-propynyl]-$\Delta^{4,9}$-estradiene-17β-ol-3-one 4.77 g of potassium carbonate and then 9.49 g of 2,4-bis(1-pyrrolidinyl)-6-(1-piperazinyl)-pyrimidine (prepared according to Patent No. WO 8,701,706) were added to a solution of 7.98 g of 17α-(3-bromo-1-propynyl)-11β-[4-dimethylamino)-phenyl]-$\Delta^{4,9}$-estradiene-17β-ol-3-one (obtained in Preparation 1) in 100 ml of acetone an the mixture was stirred for 2 hours at room temperature, then diluted with water. The product was extracted with methylene chloride and the organic phase was evaporated to dryness under reduced pressure. The dry extract was chromatographed on silica (eluent: ethyl acetate-cyclohexane (8:2)) to obtain 6.12 g of the desired product which was chromatographed again on silica (eluent: ethyl acetate/cyclohexane-isopropanol 80:20:4)) to obtain 5.5 g of desired product with a specific rotation of $[\alpha]_D = +103°5 \pm 3°$ (c=0.5% in EtOH)

Analysis: for $C_{45}H_{59}O_2N_7$
Calculated: % C 74.04, % H 8.15, % N 13.43.
Found: 74.1, 8.2, 13.2.
IR Spectrum (CHCl₃)

| Dienone | 1654 cm$^{-1}$ |
| | 1611 cm$^{-1}$ |
| | 1518 cm$^{-1}$ |

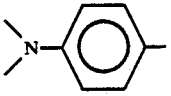

| Absorption values | 1562 cm⁻¹ |
| of the copula | 1355 cm⁻¹ |
|  | 1453 cm⁻¹ |
|  | 1445 cm⁻¹ |
|  | 1437 cm⁻¹ |

EXAMPLE 2

11β-[4-(dimethylamino)-phenyl]-17α-[3-{4-[2,6-bis(1-pyrrolidinyl)-4-pyrimidinyl]-1-piperazinyl}-1-propynyl]-Δ$^{4,9}$-estradien-17β-ol-3-one methane sulfonate 11.6 ml of a 0.3M solution of methane sulfonaic acid in ethyl acetate were added slowly to a solution of 2.57 g of the product of Example 1 in 30 ml of ethyl acetate and the solvent was evaporated under reduced pressure. The residue was taken up in 2 ml of ethanol and 10 ml of isopropyl ether were added to the solution obtained. The mixture was sirred for 30 minutes and 2.74 g of the expected product was drained. 2.425 g of the latter were crystallized by dissolution in 7.5 ml of methylene chloride and precipitation by the slow addition of 40 ml of isopropyl ether yielded 2.14 g of the desired product melting at 194° C.

Analysis for $C_{46}H_{63}N_7SO_5$
Calculated: % C 66.88, % H 7.69, % N 11.87, % S 3.88.
Found: 66.5, 7.6, 11.7, 4.8.
IRA Spectrum (CHCl₃)

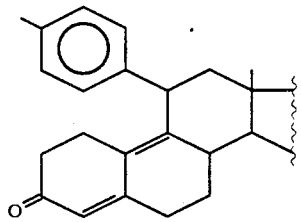

1654 cm⁻¹
1611 cm⁻¹
1518 cm⁻¹

EXAMPLE 3

11β-[4-(dimethylamino)-phenyl]-17α-[3-{4-[5,6-bis(diethylamino)-2-pyridyl]-1-piperazinyl}1-propynyl]-Δ$^{4,9}$-estradiene-17β-ol-3-one 2.16 g of 17α-(3-bromo-1-propynyl)-11β-[4-(dimethylamino)phenyl]-Δ$^{4,9}$-estradien-17β-ol-3-one (obtained in Preparation 1), 40 ml of acetone, 2.7 g of N,N,N',N'-tetraethyl-6-(1-piperazinyl)-2,3-pyridinediamine (prepared according to Patent No. WO 8,701,706 and 1.27 g of potassium carbonate were stirred for 1 hour at room temperature. The mixture was filtered and the filtrate was concentrated to dryness under reduced pressure. The residue was chromatographed on silica (eluent: ethyl acetate cyclohexane (8:2) to obtain 2.9 g of desired product with a specific rotation of [α]$_D$= +93°±3° (c=0.5% in EtOH)

Analysis for $C_{46}H_{64}N_6O_2$
Calculated: % C 75.37, % H 8.80, % N 11.46.
Found: 75.6, 8.9, 12.2.
IR Spectrum (CHCl₃)

| OH | 3600 cm⁻¹ |
| Dienone | 1654 cm⁻¹ |
|  | 1612 cm⁻¹ |

|  | 865 cm⁻¹ |
| Conjugated system due | 1587 cm⁻¹ |
| to the reagent | 1565 cm⁻¹ |
|  | 1478 cm⁻¹ |

Aromatic 1518 cm⁻¹ (F) type φ—N⟨

EXAMPLE 4

17α-[3-{4-[3,6-bis(diethylamino)-2-pyridyl]-1]-piperazinyl}-1-propynyl]-11β-[4-(dimethylamino)-phenyl-Δ$^{4,9}$-estadiene-17β-ol-3-one Using the procedure of Example 1, 3.42 g of 17α-(3-bromo-1-propynyl)-11β-[4-dimethylamino)-phenyl]-Δ$^{4,9}$-estradien-17β-ol-3-one (obtained in Preparation 1) and 4.29 g of N,N,N',N'-tetraethyl-6-(1-piperazinyl)-2,5-pyridine-diamine prepared according to U.S. Pat. No. 8,903,740 and Step B of Preparation 3 to obtain 2.18 g of the desired product with a specific rotation of [α]$_D$= +59°±2°5 (c=0.5% in EtOH)

Analysis for $C_{46}H_{64}N_6O_2$
Calculated: % C 75.37, % H 8.80, % N 11.46.
Found: 75.5, 8.9, 11.6.
IR Spectrum (CHCl₃)

| OH | 3600 cm⁻¹ |
| Dienone | 1654 cm⁻¹ |
|  | 1611 cm⁻¹ |
|  | 1518 cm⁻¹ |

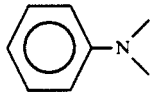

| 1595 cm⁻¹ | Absorption values |
| 1561 cm⁻¹ | of the copula |
| 1486 cm⁻¹ |  |

EXAMPLE 5

17α-[3-{4-[2,6-bis(1-pyrrolidinyl)-4-pyrimidinyl]-1-piperazinyl}-1-propenyl]-11β-[4-(dimethylamino)-phenyl]-Δ$^{4,9}$-estradien-17β-ol-3-one A mixture of 2.2 g of the product of Example 2, 140 ml of ethanol, 3 ml of triethylamine and 0.2 g of palladium at a content of 10% on barium sulfate was subjected for 4 hours to a hydrogenation at a pressure of 1261 mm of mercury. The catalyst was filtered off and washed and the solvents were distilled under reduced pressure to obtain 2.5 g of yellow foam. After purification by chromatography on silica (eluent: ethyl acetate/cyclohexane (8:2) and 2% of isopropanol), the expected product was obtained.

IR Spectrum (CHCl₃)

| Conjugated ketone | 1654 cm⁻¹ |
| Heteroaromatic | 1612 cm⁻¹ |
| Aromatic | 1563 cm⁻¹ |
|  | 1555 cm⁻¹ |
|  | 1518 cm⁻¹ |

UV Spectrum:

| 1) | In EtOH | | |
|---|---|---|---|
| | Max 233 nm $E_1^1$ = 726 | $\epsilon$ = 53,100 | |
| | Max 288 nm nm $E_1^1$ = 387 | $\epsilon$ = 28,300 | |
| | Inf. 260, 305, 330. | | |
| 2) | In EtOH, HCl, 0.1 N | | |
| | Max 244 nm $E_1^1$ = 446 | $\epsilon$ = 32,600 | |
| | Max 300 nm $E_1^1$ = 543 | $\epsilon$ = 39,700 | |
| | Inf. 218 nm. | | |

EXAMPLE 6

17α-[3-{4-[2,6-(1-pyrrolidinyl)-4-pyrimidinyl]-1-piperazinyl}-11β-[4-(diemthylamino)-phenyl]-Δ$^{4,9}$-estradien-17β-ol-3-one

STEP A:

17α-[3-{-4-[2,6-bis(1-pyrrolidinyl)-4-pyrimidinyl]-1-piperazinyl}-1-propynyl]-11β-[4-(dimethylamino)-phenyl]-3,3-(ethanediylbisoxy)-Δ$^9$-estrene-5α,17β-diol 3.54 g of 2,4-bis(1-pyrrolidinyl)-6-(1-piperazinyl)-pyrimidine were reacted under the conditions described in Example 1 with 3,3-(ethanediylbisoxy)-11-(4-dimethylaminophenyl)-17α-(3-bromo-1-propynyl)-Δ$^9$-estrene-5α,17β-diol. (Preparation 2 from 4 g of the corresponding 17α-(3-hydroxy-1-propynyl)-product to obtain 5.26 g of the expected product.

IR Spectrum (CHCl$_3$)

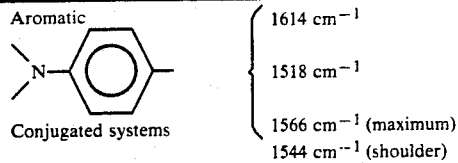

| | |
|---|---|
| Aromatic | 1614 cm$^{-1}$ |
| | 1518 cm$^{-1}$ |
| Conjugated systems | 1566 cm$^{-1}$ (maximum) |
| | 1544 cm$^{-1}$ (shoulder) |

STEP B:

17α-[3-{4-[2,6-bis(1-pyrrolidinyl)-4-pyrimidinyl]-1-piperazinyl}-1-propyl]-11β-[4-(dimethylamino)-phenyl]-3,3-(ethanediylbisoxy)-Δ$^9$-estrene-5α,17β-diol A mixture of 5.26 g of the product of Step A, 250 ml of ethanol and 2 g of palladium at a content of 10% on barium sulfate were subjected for 3 hours to a hydrogenation at 1250 mm of mercury. 2 g of catalyst were then added and hydrogenation was continued for 2 hours and after filtration and purification, 5.17 g of the expected product were obtained.

IR Spectrum (CHCl$_3$)

| OH | 3616 cm$^{-1}$ |
|---|---|
| Aromatic | 1564 cm$^{-1}$ |
| | 1554 cm$^{-1}$ |
| | 1518 cm$^{-1}$ |
| | 1469 cm$^{-1}$ |

STEP C:

17α-[3-{4-[2,6-bis(1-pyrrolidinyl)-4-pyrimidinyl]-1-piperazinyl}-1-propyl]-11β-[4-(dimethylamino)-phenyl]-Δ$^{4,9}$-estradien-17β-ol-3-one 5.17 g of the product of Step B were stirred at room temperature in 100 ml of ethanol and 100 ml of hydrochloric acid After neutralization, drying and purification followed by filtration on silica under the usual conditions, 1.94 g of the expected product were obtained with a specific rotation of $[\alpha]_D = +108° \pm 3°$ (c=0.45% in EtOH)

IR Spectrum (CHCl$_3$)

| Dienone | 1654 cm$^{-1}$ |
|---|---|
| Conjugated system | 1611 cm$^{-1}$ |
| Aromatics | 1581 cm$^{-1}$ |
| Heterocycles | 1545 cm$^{-1}$ |
| | 1518 cm$^{-1}$ |

PHARMACOLOGICAL STUDY

I—Antioxidant activity

The antioxidant activity was tested in vitro by the test of formation of malondialdehyde (MDA) which measures lipid peroxidation triggered: either a) non-enzymatically by ferrous sulfate, in 1) brain homogenates, or 2) rat liver microsomes or b) enzymatically by NADPH and carbon tetrachloride in rat liver microsomes.

1.1-MDA formation was measured on 10-fold diluted (V/V) homogenates of brains of S-D (200 g), prepared in Krebs buffer pH 7.4 by the conditions described in J. Biol. Chem. Vol., 262 (1987), p. 10438 to 10440. 1 ml of homogenate was incubated for 60 minutes at 37° C. in the presence of 25 microliters of ethanol or water or a mixture of the two, depending on the product, containing or not containing the test product, after the addition of 25 microliters of ferrous sulfate solution prepared immediately before use in water outgassed with argon (200 microliters final). 0.25 ml of incubated mixture was withdrawn and 1.5 ml of 1% strength phosphoric acid, 0.25 ml of a solution containing 200 microliters of deferoxamine (Desferal ®, Ciba Geigy) in water, 10 microliters of butylated hydroxytoluene (BHT) at a concentration of 8.7 mg/ml in ethanol and 0.5 ml of thiobarbituric acid (TBA) at a concentration of 0.6% in water were added. The mixture was heated to 100° C. for 45 minutes and cooled. 4 ml of n-butanol were added and the mixture was centrifuged for 15 minutes at 4000 rpm and the OD of the supernatant fraction was then read at 535 nm. The reaction blanks in the absence of Fe$^{++}$ were incubated under the same conditions. The percentage inhibition was calculated as follows:

$$\text{percentage inhibition} = \frac{\text{OD in the presence of product}}{\text{OD in the absence of product}}$$

| Concentration test product | percentage of inhibition | | |
|---|---|---|---|
| | $5 \times 10^{-4}$ M | $1 \times 10^{-4}$ M | $1 \times 10^{-5}$ M |
| product of Example 1 | 47.5 ± 8.8 | 42.6 ± 7.5 | 9.9 ± 6.4 |
| product of Example 2 | 60.9 ± 3.3 | 59.6 ± 4.4 | 16.0 ± 5.0 |
| product of Example 3 | 59.1 ± 3.2 | 49.2 ± 2.3 | 32.6 ± 10.1 |
| product of Example 4 | 71.8 ± 10.2 | 58.9 ± 10.9 | 48.6 ± 6.2 |

1.2-MDA formation was measured on liver microsomes of S-D rats (200 g) prepared from the fraction sedimented at 100,000 G of a liver homogenate in a sucrose buffer, of which the fraction remaining insoluble at 100,000 G in 100 mM sodium pyrophosphate buffer pH 7.4 was used and which was homogenized in 100 mM sodium phosphate buffer pH 7.4 containing 20% of glycerol and then stored at −80° C.

The microsomes were incubated for 15 minutes at 37° C. in 1 ml containing 35 mM Tris-HCl buffer/0.1M KCl pH 7.4, 1 mg of microsomal protein, 5 microliters of ethanol containing or not containing the test product and 250 microliters of ascorbate solution in the Tris buffer (0.5 mM final), after the addition of 250 microliters of ferrous sulfate prepared immediately before use in the Tris buffer (6 microliters final). The reaction was stopped by adding 2 ml of a 1M solution of trichloroacetic acid in 0.25M hydrochloric acid containing 0.4% of thiobarbituric acid. The mixture was heated to 85° C. for 25 minutes, cooled and centrifuged for 15 minutes at 3500 rpm, and the OD of the supernatant fraction was then read at 535 nm. The reaction blanks in the absence of $Fe^{++}$ were performed at the same time and the percentage inhibition was calculated as above.

| concentration test product | Percentage of inhibition | | | |
|---|---|---|---|---|
| | $1 \times 10^{-5}$ M | $5 \times 10^{-6}$ M | $1 \times 10^{-6}$ M | $1 \times 10^{-7}$ M |
| product of Example 1 | 76 ± 0.8 | 47 | 4 ± 0.6 | |
| product of Example 2 | 98.5 | 91 | 48 ± 1 | |
| product of Example 3 | 99.9 | 99.5 | 78.2 ± 0.9 | 5.2 ± 1 |
| product of Example 4 | 99.5 | 99.4 | 70 ± 2 | 0 ± 2 |

2-MDA formation was measured on liver microsomes of rats pretreated with phenobarbital (80 mg/kg in 3 i.p. injections), prepared as described above. The microsomes were incubated for 15 minutes at 37° C. in 1 ml containing 0.1M pH 7.4 phosphate buffer, 1 mg of microsomal protein, 5 microliters of ethanol containing or not containing the test product and 5 microliters of carbon tetrachloride (5.5 mM final) after the addition of 50 microliters of NADPH solution in the phosphate buffer (1 mM final). The reaction was stopped and the assay was then performed under the conditions described above.

| concentration test product | percentage of inhibition | | |
|---|---|---|---|
| | $1 \times 10^{-5}$ M | $5 \times 10^{-6}$ M | $1 \times 10^{-6}$ M |
| product of Example 1 | 72 ± 3 | 58 ± 5 | 14 ± 4 |
| product of Example 2 | 91 ± 3 | 82 ± 3 | 28 ± 3 |
| product of Example 3 | 97 | 88 ± 2 | 40 ± 1 |
| product of Example 4 | 888 ± 1 | 85 ± 2 | 48 ± 3 |

II—Detoxifying activity in vivo

The detoxifying activity after intoxication associated with lipid peroxidaton was tested for by measurement of the mortality induced in rats by ferric nitrilotriacetate (NTA-$Fe^{+++}$) intoxication. A solution of NTA-$Fe^{+++}$ complex was prepared immediately before use, suspended in sesame oil and injected intraperitoneally at doses of 5, 10 or 15 mg of iron/kg of body weight into non-fasted Wistar male rats weighing approximately 200 g. The survival rate of rats which received a prior injection of the test product at a dose of 5 mg/kg intraperitoneally, 30 minutes before the injection of 15 mg/kg of poison was determined. Whereas none of the animals treated with the poison alone survived after 4 hours, 20% of the animals pretreated with the product of Example 2 were still alive 15 days later.

III—Anti-inflammatory activity

The anti-inflammatory activity was assessed in vivo by measurement of the anti-oedematous activity in the test of arachidonic acid-induced plantar oedema described by Di Martino et al. (Agents and Actions, 1987 21 3/4 303). The experimental animals were Sprague-Dawley strain SPF male rats weighing 150 to 170 g (Iffa Credo).

This test was performed on groups of 8 male rats weighing 130 to 150 g, fasted for 16 hours. Arachidonic acid was injected under the plantar aponeurosis of one hindfoot at a dose of 0.2 mg in a volume of 0.1 ml. The volume of the foot was measured using a water plethysmometer before and 1 hour after the injection of arachidonic acid. The difference between these two volumes represented the degree of inflammation. The animals were treated with the test products or the vehicle alone at the same time as the injection of arachidonic acid. The test products were administered orally in a volume of 4 ml/kg after being suspended in 0.5% strength methyl cellulose. All the experiments were carried out with dexamethasone administered orally at a dose of 0.5 mg/kg as reference product.

The results were expressed as a change in volume of the foot 1 hour after the injection of arachidonic acid (AA) in the absence or in the presence of the test product administered at different doses. Statistical interpretation of the results was performed according to Dunnett's test (*$p<0.05$—**$p<0.1$) or according to the Mann-Whitney test ($^o p<0.05$—$^{\infty}p<0.01$). For each dose administered orally, the percentage inhibition of the oedema by the test product was calculated relative to the control.

| | Dose mg/kg | Change in volume of the foot 1 hour after AA ($cm^3$) (mean ± s.e.m.) | % inhibition |
|---|---|---|---|
| Controls | 0 | 0.58 ± 0.03 | |
| Product of Example 3 | 1 | 0.48 ± 0.05** | −17 |
| | 4 | 0.43 ± 0.06** | −27 |
| | 20 | 0.40 ± 0.04** | −31 |

The product of Example 3 manifests a significant anti-inflammatory activity at low doses and under the same experimental conditions, dexamethasone induced a 30 to 40% inhibition of the oedema at a dose of 0.5 mg/kg.

Various modifications of the compounds and method of the invention may be made without departing from the spirit or scope thereof and it should be understood that the invention is intended to be limited only as defined in the appended claims.

What we claim is:

1. A compound selected from the group consisting of a compound of the formula

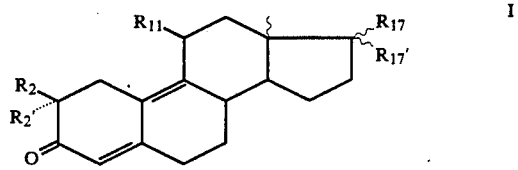

wherein R₂ and R'₂ are individually hydrogen or methyl, R₁₁ is an organo radical of 1 to 18 carbon atoms with the atom adjacent to the 11-carbon atom being a carbon and selected from the group consisting of a) phenyl and phenylalkyl optionally substituted with at least one member of the group consisting of alkyl and alkoxy of 1 to 4 carbon atoms, alkenyloxy of 2 to 4 carbon atoms, halogen, —OH, —CF₃, alkylthio of 1 to 4 carbon atoms with the sulfur optionally oxidized, acyl of an organic carboxylic acid, —NH₂ and mono and dialkylamino of 1 to 8 carbon atoms, and an heterocycle selected from morpholino or piperidyl, b) an heterocycle selected from the group consisting of thienyl, furyl, isothienyl, isofuryl, thiazolyl, isothiazolyl, oxazolyl, isoxazolyl, thiadiazolyl, pyridyl or piperidyl,

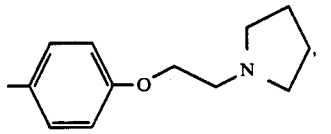

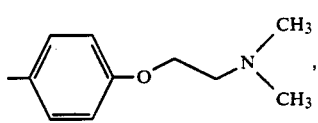

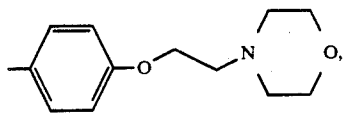

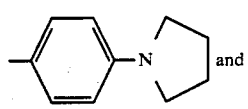

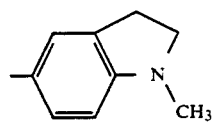

the wavy lines at the 13 and 17-positions indicate that when the 13-methyl is α, R'₁₇ group is β and R₁₇ is α and when the 13-methyl is β, R₁₇ is β and R'₁₇ is α, R₁₇ is —OH or acyloxy of 1 to 18 carbon atoms and R'₁₇ is

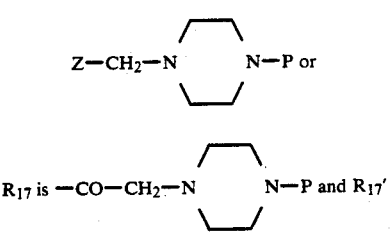

is hydrogen or —OH or acyloxy of 1 to 18 carbon atoms, Z is selected from the group consisting of a single bond, alkylene of 1 to 5 carbon atoms and alkenylene and alkynylene of 2 to 5 carbon atoms and p is selected from the group consisting of pyrimidinyl and pyridyl optionally substituted with 1 or 2 individual members of the group consisting of amino, alkylamino and dialkylamino of 1 to 4 alkyl carbon atoms and aminated 5- or 6-membered heterocycle selected from the group consisting of pyrrolidine, piperidine, pyrrole, pyridyl and pyrimidinyl optionally substituted with alkyl of 1 to 3 carbon atoms and its non-toxic, pharmaceutically acceptable acid addition salts.

2. A compound of claim 1 wherein P is pyrimidinyl or pyridyl substituted with 1 or 2 individual members of dialkylamino or aminated 5- or 6-membered heterocycles.

3. A compound of claim 1 wherein P is selected from the group consisting of 2,6-bis(1-pyrrolidinyl)-4-pyrimidinyl, 5,6-bis(diethylamino)-2-pyridyl and 3,6-bis(diethylamino)-2-pyridyl.

4. A compound of claim 1 wherein the 13-methyl is β.

5. A compound of claim 1 wherein R₁₁ is aryl or aralkyl substituted with an amino of the formula

wherein R' and R" are alkyl of 1 to 8 carbon atoms or a primary, secondary or tertiary alkyl of 1 to 8 carbon atoms containing at least one nitrogen heteroatom and optionally at least one nitrogen, —O— or —S— heteroatom or substituted with a heterocycle containing at least one nitrogen atom.

6. A compound of claim 1 wherein R₁₁ is selected from the group consisting of 2-, 3- or 4-pyridyl,

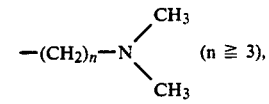

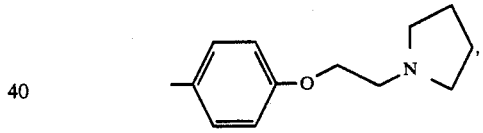

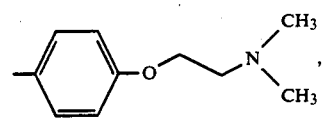

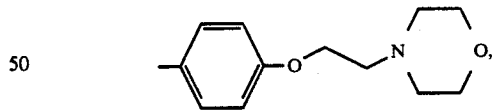

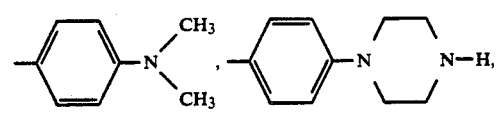

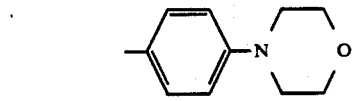

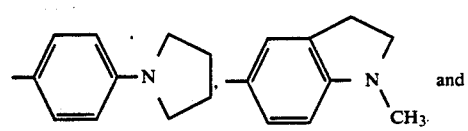

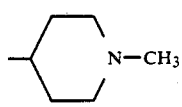

7. A compound of claim 1 wherein $R_{11}$ is selected from the group consisting of thienyl, furyl, cycloalkyl of 3 to 6 carbon atoms, phenyl and phenyl substituted with at least one member of the group consisting of —OH, halogen, —CF$_3$, alkyl, alkoxy and alkylthio optionally oxidized to sulfoxide or sulfone.

8. A compound of claim 1 wherein $R_{11}$ is phenyl substituted with at least one member of the group consisting of chlorine, fluorine, methylthio, methylsulfonyl, methoxy, —OH, alkoxy and acyl.

9. A compound of claim 1 wherein $R_2$ and $R_2'$ are hydrogen.

10. A compound of claim 1 wherein $R_{17}$ is —OH and $R_{17}'$ is

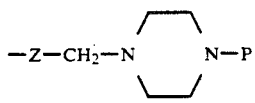

11. A compound of claim 1 wherein $R_{17}'$ is

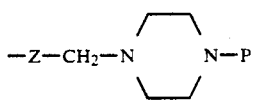

and Z is selected from the group consisting of —CH$_2$—CH$_2$—, —CH=CH— and —C≡C—.

12. A compound of claim 1 selected from the group consisting of 11β-[4-(dimethylamino)-phenyl]-17α-[3-{4-[2,6-bis(1-pyrrolidinyl)-4-pyrimidinyl]-1-piperazinyl}-1-propynyl]-Δ$^{4,9}$-estradien-17β-ol-3-one; 11β-[4-(dimethylamino)-phenyl]-17α-[3-{4-[5,6-bis(diethylamino)-2-pyridyl]-1-piperazinyl}-1-propynyl]-Δ$^{4,9}$-estradien-17β-ol-3-one; 11β-[4-(dimethylamino)-phenyl]-17α-[3-{4-[3,6-bis(diethylamino)-2-pyridyl]-1-piperazinyl}-1-propynyl]-Δ$^{4,9}$-estradien-17β-ol-3-one; 11β-[4-(dimethylamino)-phenyl]-17α-[3-{4-[2,6-bis(1-pyrrolidinyl)-4-pyrimidinyl]-1-piperazinyl}-1-propenyl]-Δ$^{4,9}$-estradien-17β-ol-3-one and 11β-[4-(dimethylamino)-phenyl]-17α-[3-{4-[2,6-bis(1-pyrrolidinyl)-4-pyrimidinyl]-1-piperazinyl}-1-propyl]-Δ$^{4,9}$-estradien-17β-ol-3-one and their non-toxic, pharmaceutically acceptable acid addition salts.

13. A compound having a formula selected from the group consisting of

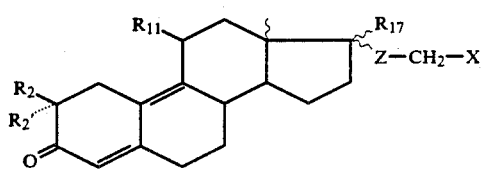

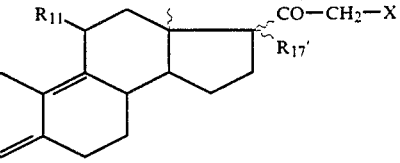

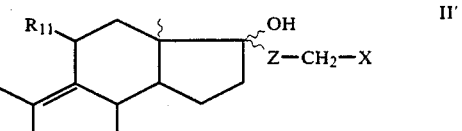

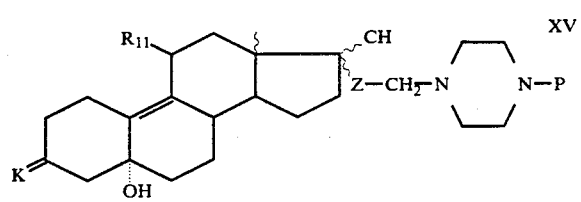

wherein $R_2'$, $R_2$, $R_{11}$, P, Z, $R_{17}$ and $R_{17}'$ and the wavy lines have the definitions of claim 1, X is halogen and K is ketone protecting group.

14. A compound of claim 13 selected from the group consisting of 17α-(3-bromo-1-propynyl)-11β-[4-(dimethylamino)-phenyl]-Δ$^{4,9}$-estradien-17β-ol-3-one and 3,3-(ethanediylbisoxy)-17α-(3-bromo-1-propynyl)-11β-[4-(dimethylamino)-phenyl]-Δ$^9$-estrene-5α,17β-diol.

15. An anti-oxidant composition comprising an antioxidantically effective amount of at least one compound of claim 1 and its non-toxic, pharmaceutically acceptable acid addition salts.

16. A composition of claim 15 wherein the active compound is selected from the group consisting of 11β-[4-(dimethylamino)-phenyl]-17α-[3-{4-[2,6-bis(1-pyrrolidinyl)-4-pyrimidinyl]-1-piperazinyl}-1-propynyl]-Δ$^{4,9}$-estradien-17β-ol-3-one; 11β-[4-(dimethylamino)-phenyl]-17α-[3-{4-[5,6-bis-(diethylamino)-2-pyridyl]-1-piperazinyl}-1-propynyl]-Δ$^{4,9}$-estradien-17β-ol-3-one; 11β-[4-(dimethylamino)-phenyl]-17α-[3-{4-[3,6-bis(diethylamino)-2-pyridyl]-1-piperazinyl}-1-propynyl]-Δ$^{4,9}$-estradien-17β-ol-3-one;. 11β-[4-(dimethylamino)-phenyl]-17α-[3-{4-[2,6-bis(1-pyrrolidinyl)-4-pyrimidinyl]-1-piperazinyl}-1-propenyl]-Δ$^{4,9}$-estradien-17β-ol-3-one and 11β-[4-(dimethylamino)-phenyl]-17α-[3-{4-[2,6-bis(1-pyrrolidinyl)-4-pyrimidinyl]-1-piperazinyl}-1-propyl]-Δ$^{4,9}$-estradien-17β-ol-3-one and their non-toxic, pharmaceutically acceptable acid addition salts.

17. A method of inducing anti-oxidant activity in warm-blooded animals comprising administering to a warm-blooded animal an anti-oxidantically effective amount of at least one compound of claim 1.

18. The method of claim 17 wherein the active compound is selected from the group consisting of 11β-[4-(dimethylamino)-phenyl]-17α-[3-{4-[2,6-bis(1-pyrrolidinyl)-4-pyrimidinyl]-1-piperazinyl}-1-propynyl]-Δ$^{4,9}$-estradien-17β-ol-3-one; 11β-[4-(dimethylamino)-phenyl]-17α-[3-{4-[5,6-bis-(diethylamino)-2-pyridyl]-1-piperazinyl}-1-propynyl]-Δ$^{4,9}$-estradien-17β-ol-3-one; 11β-[4-(dimethylamino)-phenyl]-17α-[3-{4-[3,6-bis(diethylamino)-2-pyridyl]-1-piperazinyl}-1-propynyl]-Δ$^{4,9}$-estradien-17β-ol-3-one; 11β-[4-(dimethylamino)-phenyl]-17α-[3-{4-[2,6-bis(1-pyrrolidinyl)-4-pyrimidinyl]-1-piperazinyl}-1-propenyl]-Δ$^{4,9}$-estradien-17β-ol-3-one and 11β-[4-dimethylamino)-phenyl]-17α-[3-{4-[2,6-bis(1-pyrrolidinyl)-4-pyrimidinyl]-1-piperazinyl}-1-propyl]-Δ$^{4,9}$-estradien-17β-ol-3-one and their non-toxic, pharmaceutically acceptable acid addition salts.

* * * * *